US010182743B2

(12) United States Patent
Johnson

(10) Patent No.: US 10,182,743 B2
(45) Date of Patent: Jan. 22, 2019

(54) MOBILITY ASSESSMENT DEVICE

(76) Inventor: Norman L. Johnson, Pittsburgh, PA (US)

( * ) Notice: Subject to any disclaimer, the term of this patent is extended or adjusted under 35 U.S.C. 154(b) by 1336 days.

(21) Appl. No.: 12/910,006

(22) Filed: Oct. 22, 2010

(65) Prior Publication Data

US 2011/0098607 A1    Apr. 28, 2011

Related U.S. Application Data

(60) Provisional application No. 61/254,782, filed on Oct. 26, 2009.

(51) Int. Cl.
| A61B 5/103 | (2006.01) |
| A61B 5/11 | (2006.01) |
| A61B 5/00 | (2006.01) |
| A63B 6/00 | (2006.01) |
| A63B 21/00 | (2006.01) |
| A63B 71/06 | (2006.01) |

(52) U.S. Cl.
CPC .......... *A61B 5/1038* (2013.01); *A61B 5/1118* (2013.01); *A61B 5/1126* (2013.01); *A61B 5/68* (2013.01); *A61B 5/6887* (2013.01); *A63B 6/00* (2013.01); *A63B 21/4037* (2015.10); *A63B 2071/0694* (2013.01)

(58) Field of Classification Search
CPC .................................................. A61B 5/103
USPC ........ 600/595; 463/31, 42; 473/257; 482/41, 482/15
See application file for complete search history.

(56) References Cited

U.S. PATENT DOCUMENTS

| 4,733,864 A | 3/1988 | Casteel |
| 5,567,497 A | 10/1996 | Zegler et al. |
| 5,667,873 A | 9/1997 | Beckenbach |
| 6,293,026 B1 * | 9/2001 | Lee et al. ......................... 33/512 |
| 6,410,835 B2 * | 6/2002 | Suzuki et al. ............... 84/464 R |
| 6,844,058 B2 | 1/2005 | Blum et al. |
| 7,250,847 B2 * | 7/2007 | Wagner ........................ 340/10.1 |
| 2004/0009845 A1 | 1/2004 | Johnson |
| 2008/0146329 A1 * | 6/2008 | Kodama et al. ................ 463/31 |
| 2009/0110820 A1 | 4/2009 | Kessler et al. |

(Continued)

OTHER PUBLICATIONS

Rebecca J. Hess, Jennifer S. Brach, Sara R. Piva and Jessie M. Vanswearingen; Waling Skill Can Be Assessed in Older Adults: Validity of the Figure-of-8 Walk Test; Jan. 2010; vol. 90; www.ptjournal.org.

(Continued)

*Primary Examiner* — Daniel L Cerioni
*Assistant Examiner* — Yasmeen S Warsi
(74) *Attorney, Agent, or Firm* — AP Patents

(57) ABSTRACT

The present invention in several embodiments is a mobility assessment device which is easy to use and which will aid practitioners in evaluating a patients' mobility. The mobility assessment device of the present invention is preferably constructed from a skid resistant high contrast material that can easily be folded, rolled or stored in a compact space. The mobility assessment device of the present invention may include markings or indicia to aid a patient in properly performing one or several mobility assessment tests. The included indicia may have measurements and other marking for aiding a medical professional in evaluating a patient's mobility.

13 Claims, 2 Drawing Sheets

(56) References Cited

U.S. PATENT DOCUMENTS

2009/0181836 A1* 7/2009 Schneider .................. 482/140
2010/0049095 A1* 2/2010 Bunn et al. ................. 600/595

OTHER PUBLICATIONS

Anne Shumway-Cook, Sandy Brauer, Marjorie Woollacott; Predicting the Probability for Falls in Community-Dwelling Older Adults Using the Timed Up & Go Test; Sep. 2000; vol. 80 No. 9; Physical Therapy Research Report.

Susan L. Whitney, Gregory F. Marchetti, Laura O. Morris, Patrick J. Sparto; The Reliability and Validity of the Four Square Step Test for People With Balance Deficits Secondary to a Vestibular Disorder; Arch Phys Med Rehabil, vol. 88, Jan. 2007.

Stacy Fritz, Michelle Lusardi; White Paper: "Walking Speed: the Sixth Vital Sign"; Journal of Geriatric Physical Therapy, vol. 32; 2:09.

Dite, Wayne, BAppSci, GradDip, Viviene A. Temple, PhD; A Clinical Test of Stepping and Change of Direction to Identify Multiple Falling Older Adults; Arch Phys Med Rehabil vol. 83, Nov. 2002.

Rebecca J. Hess, Jennifer S. Brach, Sara R. Piva, Jessi M. Vanswearingen; Walking Skill Can Be Assessed in Older Adults: Validity of the Figure-of-8 Walk Test, Research Report Jan. 2-1—Volum 90 No. 1 Physical Therapy.

William H. Staples; The Four Square Step Test; GeriNotes vol. 18, No. 3 2011.

Anne Sumway-Cook, Sandy Brauer, Marjorie Woollacott; Predicting the Probability for Falls in Community-Dwelling Older Adults Using the Timed Up & Go Test; Research Report; Physical Therapy, vol. 80, No. 9 Sep. 2000.

Johanna Jonsdottir ScD, Davide Cattaneo PT; Reliability and Validity of the Dynamic Gait Index in Person With Chronic Stroke; Arch Phys Med Rehavil vol. 88, Nov. 2007.

* cited by examiner

MOBILITY ASSESSMENT DEVICE

CROSS REFERENCE TO RELATED APPLICATION

This patent application is related to and claims priority from U.S. Provisional Patent Application Ser. No. 61/254,782 filed Oct. 26, 2009.

FIELD OF THE INVENTION

The present invention relates, in general, to a mobility assessment device, more particularly, this invention relates to a mat with pre-selected indicia disposed thereon for use in evaluating a predetermined person's mobility.

BACKGROUND OF THE INVENTION

Prior to the conception and development of the present invention, physicians and physical therapists have observed and evaluated patients' mobility (including gait, speed, balance, etc.) as such patients perform various preselected activities such as the Four Square Step Test, Figure-of-8 Walk Test timed "up and go" tests, Dynamic Gait Index, and the like. However, it can be difficult for practitioners to make determinations by simply observing patients' movements. There is a need for a device to aid such practitioners in making their assessments.

SUMMARY OF THE INVENTION

The present invention in several embodiments is a mobility assessment device which is easy to use and which will aid practitioners in evaluating a patient's mobility. The mobility assessment device of the present invention is preferably constructed from a skid resistant high contrast material that can easily be folded, rolled or stored in a compact space.

The mobility assessment device of the present invention may include markings or indicia to aid a patient in properly performing one or several mobility assessment tests. The included indicia may have measurements and other marking for aiding a medical professional in evaluating a patient's mobility.

OBJECTS OF THE INVENTION

It is, therefore, one of the primary objects of the present invention to provide a mobility assessment device which is easy to use and which will aid practitioners in evaluating patients' mobility.

Another object of the present invention is to provide a mobility assessment device which can be used to direct a patient in moving in at least one of a predetermined direction, a series of predetermined directions, and a combination thereof for at least one of a predetermined distance, a series of predetermined distances, and a combination thereof.

Still another object of the present invention is to provide a mobility assessment device which is substantially formed as a floor mat and which can be easily stored when not in use.

Another object of the present invention is to provide a mobility assessment device which substantially formed as a floor mat having predetermined indicia disposed thereon for use in directing a predetermined person to move at least one of at least one predetermined distance, at least one predetermined direction, in at least one predetermined manner, and a combination thereof.

Yet another object of the present invention is to provide a mobility assessment device in the form of a floor mat which is at least one of flexible, foldable, and a combination thereof.

It is still another object of the present invention to provide a mobility assessment device formed substantially as a floor mat which may be placed on a floor with a chair positioned closely adjacent thereto for use in guiding a first predetermined person through a series of movements beginning with such first predetermined person sitting in such chair then moving there from to at least one of predetermined positions on such mobility assessment device, predetermined positions near such mobility assessment device, and a combination thereof, such that a second predetermined person can observe how such first predetermined person moves.

It is yet another object of the present invention to provide a mobility assessment device formed substantially as a flexible substantially flat mat having a length of about 21 feet and a width of about 3 and ½ feet, with indicia disposed thereon indicating the length of the mat at about 5 feet, about 6 feet, about 10 feet, about 12 feet, about 15 feet, about 20 feet, and further having indicia disposed thereon within the first five feet in length depicting a first plurality of arrows formed to illustrate a first square having a first predetermined size and having the numerals 5, 6, 7, and 8 each disposed within a predetermined interior corner of such first square, and having indicia disposed within such first square illustrating a second square having a second predetermined size, such indicia being formed as second set of arrows formed to illustrate sides such second square and having the numerals 1, 2, 3, and 4 each disposed within a predetermined interior corner of such second square, such second square further having indicia disposed within such second square to indicate a center point thereof, such mobility assessment tool being for use in directing a first predetermined person through a series of movements such that a second predetermined person can observe how such first predetermined person moves.

In addition to the various objects and advantages of the present invention described with some degree of specificity above it should be obvious that additional objects and advantages of the present invention will become more readily apparent to those persons who are skilled in the relevant art from the following more detailed description of the invention.

Figure 1:
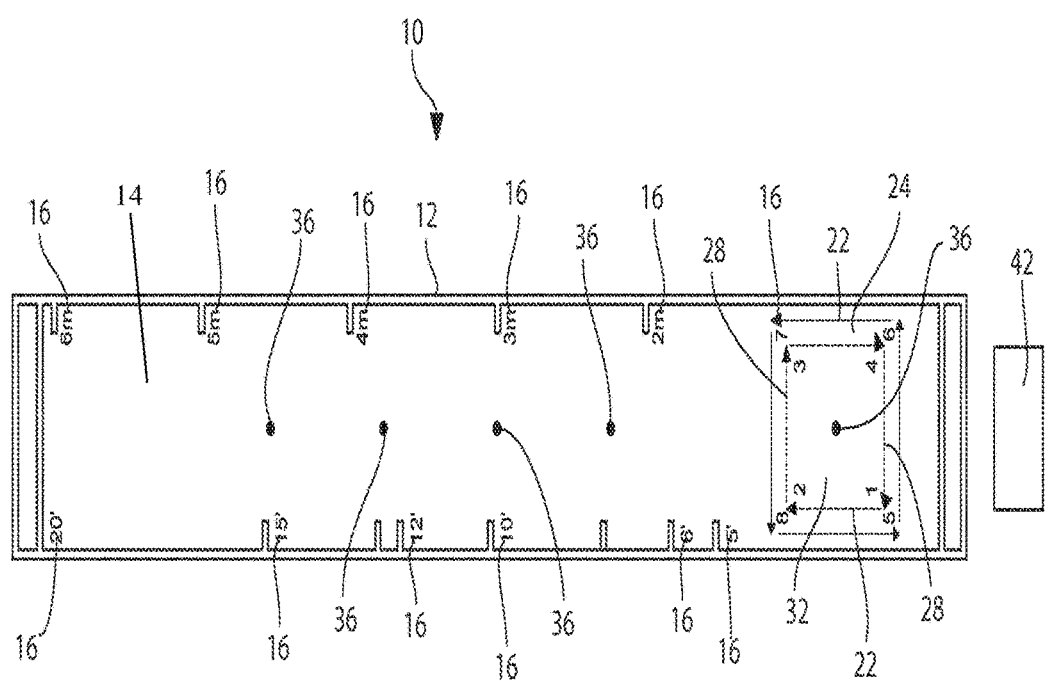
FIG. 1 is a partial perspective of the invention according to one embodiment of the invention.

BRIEF DESCRIPTION OF A PRESENTLY PREFERRED AND VARIOUS ALTERNATIVE EMBODIMENTS OF THE INVENTION

Prior to proceeding to the more detailed description of the present invention it should be noted that, for the sake of clarity and understanding, identical components which have identical functions have been identified with identical reference numerals throughout the several views illustrated in the drawing figures.

Figure 2:
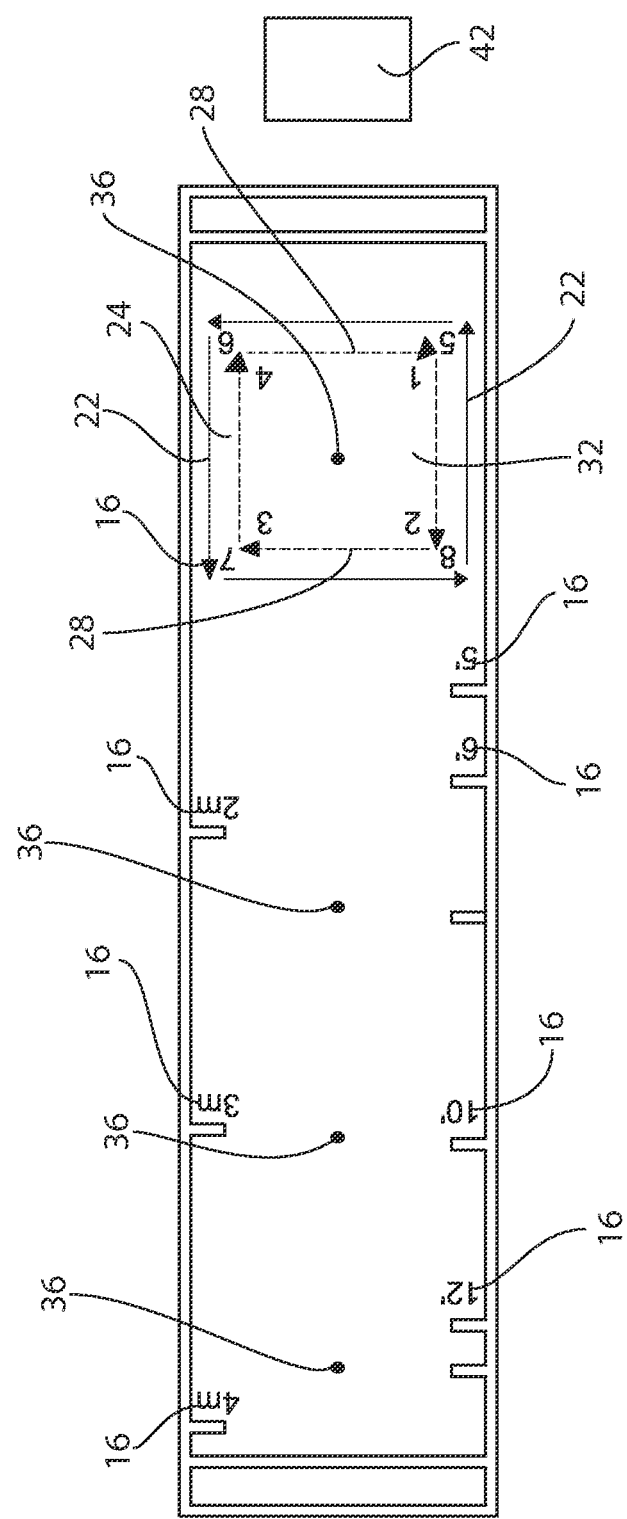
FIG. 2 is a partial perspective of the invention according to another embodiment of the invention.

Reference is now made, more particularly, to FIG. 1 and FIG. 2.
}

There is a need for a mobility assessment device which can be used by a predetermined practitioner to evaluate the mobility of a predetermined person.

Accordingly, a mobility assessment device is provided. Such mobility assessment device, generally designated 10, includes a base member 12 having a first predetermined size and a first predetermined shape and being manufactured from a first predetermined material.

It is presently preferred that such base member 12 is a mat type member. It is further presently preferred that such base member is substantially flat.

It is presently preferred that such predetermined material is manufactured from at least one of plastic, rubber, cellulose, and a combination thereof. It is presently preferred that such first predetermined material is plastic. It is presently most preferred that such first predetermined material is a projector screen material.

It is presently preferred that such first predetermined shape is substantially rectangular. It is presently preferred that such first predetermined shape is between about 170 inches and about 288 inches long, and between about 38 inches and about 64 inches wide. It is presently most preferred that such predetermined shape is between about 170 inches and 248 inches long, and about 42 inches wide.

It is presently preferred that such base member 12 includes a first side 14 and a second side (not shown). It is presently preferred that such first side 14 of such base member 12 includes predetermined indicia 16 disposed thereon. It is presently preferred that such predetermined indicia 16 includes at least one of directional markings, directional instructions, length markings, numbers, letters, words, symbols, and a combination thereof.

It is meant that such predetermined indicia 16 be useful in directing a predetermined patient (not shown) to ambulate at least one of on such mobility assessment device 10, across such mobility assessment device 10, around such mobility assessment device 10, and a combination thereof in accordance with such predetermined indicia 16.

It is presently preferred that such predetermined indicia 16 include markings indicating points where the length of such mobility assessment device 10 reaches about 5 feet, about 6 feet, about 10 feet, about 12 feet, about 15 feet, and about 20 feet. It is further presently preferred that such predetermined indicia 16 includes a first plurality of arrows 22 formed to illustrate a first square 24 having a first predetermined size and such predetermined indicia including the numerals 5, 6, 7, and 8 each disposed within predetermined interior corners of such first square 24, such predetermined indicia further includes a second set of arrows 28 disposed within such first square 24 formed to illustrate a second square 32 having a second predetermined size and such predetermined indicia 16 including the numerals 1, 2, 3, and 4 each disposed within predetermined interior corners of such second square 32, such indicia 16 further including a marking to indicate a center point 36 of such second square 32. A center point 36 can also be marked down the mobility assessment device 10 to designate the center of the width of the mobility assessment device 10.

It is meant that such mobility assessment device 10, via such predetermined indicia 16, guide a first predetermined person (such as a patient) through a series of movements as directed by a second predetermined person (such as a practitioner) such that such second predetermined person can observe how such first predetermined person moves. Such mobility assessment device 10 may be used to direct a patient in moving in at least one of a predetermined direction, a series of predetermined directions, and a combination thereof for at least one of a predetermined distance, a series of predetermined distances, and a combination thereof according to such predetermined indicia 16 during observation by such practitioner thereby enabling such practitioner to properly evaluate the mobility of such patient. Such mobility assessment device 10 may be used alone or with a chair 42 placed closely adjacent thereto to act as a starting point, and possibly as an ending point if desired, for such patient.

It is presently preferred that such mobility assessment device 10 is at least one of flexible, rollable, bendable, foldable, and a combination thereof. It is meant that such mobility assessment device 10 be compactable for storage when not in use.

It is presently preferred that such mobility assessment device 10 includes a non-skid means (not shown) disposed on such second side thereof for preventing such mobility assessment device 10 from moving when such non-skid means is adjacent a predetermined floor (not shown). It is presently preferred that such non-skid means is at least one of a rubber coating, a plurality of rubber feet, an adhesive means, and a combination thereof.

While a presently preferred and various alternative embodiments of the present invention have been described in sufficient detail above to enable a person skilled in the relevant art to make and use the same it should be obvious that various other adaptations and modifications can be envisioned by those persons skilled in such art without departing from the spirit of the invention.

The invention claimed is:

1. A method of physical therapy comprising the steps of:
providing a floor mat having indicia disposed within confines thereof, said indicia having two sets of lines, each line from each set of lines being disposed generally normal to and at each of a pair of opposite edges of said floor mat, with lines in said each set of lines being in a spaced apart relationship with each other, a distance between some lines from one set of lines is greater or smaller than a distance or distances between remaining lines from said one set of lines, two sets of arrows oriented in different directions and positioned to define an inner square and an outer square, markings and plurality of numerals, each disposed adjacent a respective arrow and adjacent a respective one of said plurality of lines and defining a specific distance from one edge disposed normal to said pair of opposite edges;
positioning a chair adjacent said one edge disposed normal to said pair of opposite edges;
moving, by a person undergoing said physical therapy, through a series of movements beginning with said person sitting in said chair, then moving therefrom to at least one of predetermined positions on said floor mat, predetermined positions near said floor mat, and a combination thereof, said series of movements including a Four Square Step Test, a Figure-of-8 Walk Test, Timed "up and go" tests, and a Dynamic Gait Index test; and
assessing, by observation of a practitioner through said series of movements, a mobility of said person undergoing said physical therapy, said mobility including gait, speed, and balance.

2. The mobility assessment device of claim 1 wherein said step of providing said floor mat includes the step of providing said floor mat being manufactured from a projector screen material.

3. A mobility assessment device consisting of:
a floor mat; and
indicia disposed within confines of said floor mat said indicia including:
- a first set of lines disposed in a spaced apart relationship with each other generally normal to and adjacent a first edge of said floor mat, a distance between some lines from said first set of lines is greater or smaller than a distance or distances between remaining lines from said first set of lines,
- a second set of lines disposed in a spaced apart relationship with each other generally normal to and adjacent a second edge of said floor mat, said second edge being opposite said first edge,
- plurality of numerals, each disposed adjacent a respective line in each of said first and second sets of lines and defining a specific distance from an edge of said floor mat disposed generally perpendicular to said pair of opposite first and second edges,
- four first arrows positioned to define a first square adjacent said edge of said floor mat disposed normal to said pair of opposite first and second edges,
- numerals 5, 6, 7 and 8, each positioned within said first square at one corner thereof,
- four second arrows positioned within said first square to define a second square,
- numerals 1, 2, 3 and 4, each positioned within said second square at one corner thereof,
- plurality of markings disposed in a spaced apart relationship with each other along said pair of opposite first and second edges to define a center line of said floor mat, wherein one of said plurality of markings is disposed within said second square to define a center point thereof, and
- whereby said indicia is configured to assess mobility of a person undergoing a physical therapy and during a series of movements of the person to perform at least one of a Four Square Step Test, a Figure-of-8 Walk Test, Timed "up and go" test(s), and a Dynamic Gait Index test within said confines of said floor mat.

4. The mobility assessment device of claim 3 wherein, said floor mat is one of a flexible, a foldable, and a combination thereof.

5. The mobility assessment device of claim 3, wherein said floor mat defines a projector screen material.

6. The mobility assessment device of claim 3 wherein, said floor mat has a length of 14 feet or 21 feet.

7. The mobility assessment device of claim 3 wherein, said floor mat has a length of 4 meters or 6 meters.

8. The mobility assessment device of claim 3 wherein, said floor mat has a width of 3 and ½feet or 1 meter.

9. The mobility assessment device of claim 3 wherein, lines from said first set of lines are disposed at a distance of 5 feet, 6 feet, 10 feet, 12 feet, 15 feet and/or 20 feet from said edge of said floor mat disposed generally perpendicular to said pair of opposite first and second edges.

10. The mobility assessment device of claim 3 wherein, lines from said second set of lines are disposed at a distance of 2 meters, 3 meters, 4 meters, 5meters and/or 6 meters from said edge of said floor mat disposed generally perpendicular to said pair of opposite first and second edges.

11. The mobility assessment device of claim 3, wherein said floor mat is at least one of flexible, foldable, and a combination thereof and wherein said indicia is disposed on one surface of said floor mat.

12. The mobility assessment device of claim 3, wherein said floor mat is defined by a projector screen.

13. The mobility assessment device of claim 11, wherein said four first arrows are oriented in a different direction than said four second arrows.

* * * * *